United States Patent [19]

King

[11] Patent Number: 5,388,584

[45] Date of Patent: Feb. 14, 1995

[54] METHOD AND APPARATUS FOR PREVENTION OF FLUID INTRUSION IN A PROBE SHAFT

[75] Inventor: Robert W. King, Lexington, Mass.

[73] Assignee: Hewlett-Packard Company, Palo Alto, Calif.

[21] Appl. No.: 228,461

[22] Filed: Apr. 15, 1994

[51] Int. Cl.⁶ ............................................... A61B 8/12
[52] U.S. Cl. ............................ 128/662.06; 174/113 R
[58] Field of Search ...................... 128/662.03, 662.06; 601/2; 174/113 R, 121 R, 121 A, 121 SR

[56] References Cited

U.S. PATENT DOCUMENTS

| Re. 27,569 | 2/1973 | Ackerman . | |
|---|---|---|---|
| 3,244,174 | 4/1966 | Wesbey et al. . | |
| 3,568,660 | 3/1971 | Crites et al. . | |
| 3,745,233 | 7/1973 | Lania et al. | 174/121 A |
| 3,823,255 | 7/1974 | La Gase et al. | 174/113 R |
| 4,590,950 | 5/1986 | Iwaszkiewicz et al. . | |
| 4,667,686 | 5/1987 | Peers-Travarton . | |
| 4,679,572 | 7/1987 | Baker, Jr. . | |
| 4,729,384 | 3/1988 | Bazenet . | |
| 4,730,389 | 3/1988 | Baudino et al. . | |
| 4,928,699 | 5/1990 | Sasai . | |
| 4,951,677 | 8/1990 | Crowley et al. . | |
| 4,991,588 | 2/1991 | Pflueger et al. . | |
| 5,020,539 | 6/1991 | Yokoi et al. . | |
| 5,156,155 | 10/1992 | King . | |

FOREIGN PATENT DOCUMENTS 0062315 10/1982 European Pat. Off. .
0234951 9/1987 European Pat. Off. .
2584288 1/1987 France .

Primary Examiner—George Manuel

[57] ABSTRACT

A shaft for an invasive bodily probe which includes a central core, a metal sheath surrounding the core and an outer elastomeric coating. A membrane formed of a textile layer disposed between two layers of a flexible, tough film is disposed between the sheath and the outer elastomeric coating. The membrane typically is formed of a woven material whose interstices have been completely filled by two layers of a urethane material. The membrane completely seals the sheath and core to protect the patient from electrical currents carried by wires within the core, and to prevent bacteria and fluids from being trapped in cuts in the shaft. The wires are also protected from damage from bodily fluids and cleaning solutions, since the core is sealed from the environment. A method for preparation of such a shaft includes the formation of a laminate comprised of a layer of a textile encapsulated between two layers of a flexible film, formation of a tube of this laminate, and the sliding of the tube over the existing core and sheath. Adhesive may be used to bond the membrane to the outer elastomeric coating.

16 Claims, 3 Drawing Sheets

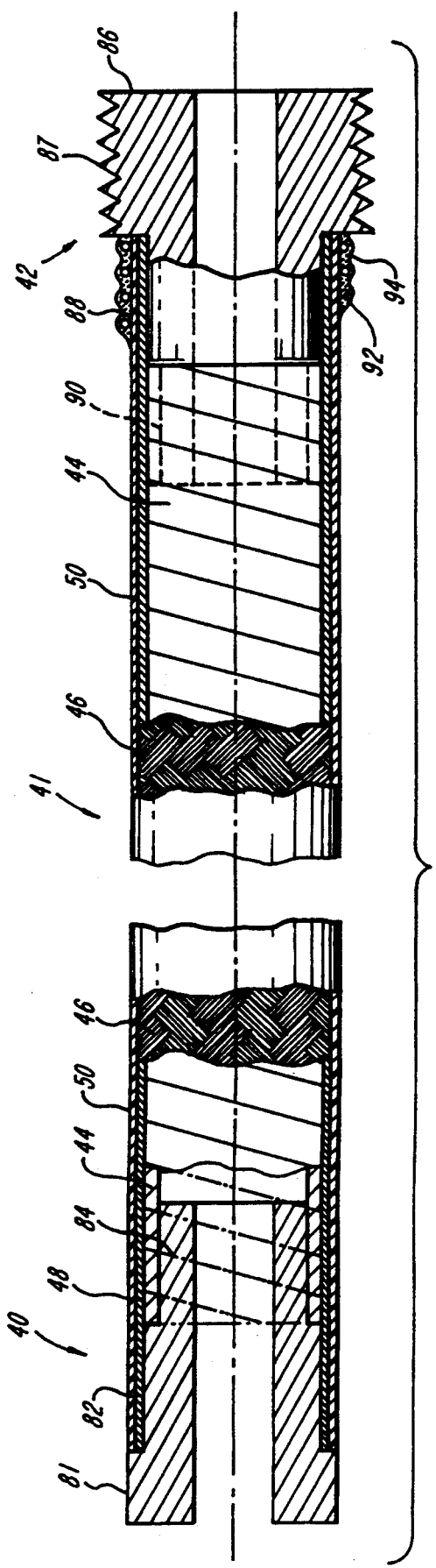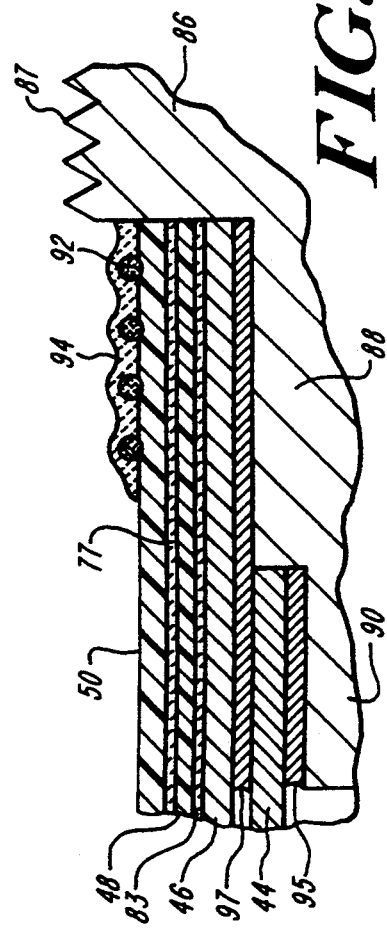

METHOD AND APPARATUS FOR PREVENTION OF FLUID INTRUSION IN A PROBE SHAFT

FIELD OF THE INVENTION

This invention relates generally to probes for use with bodily cavities, and more particularly, to a shaft structure for a transesophageal probe shaft.

BACKGROUND OF THE INVENTION

Ultrasonic transducers, and in particular, phased array ultrasonic transducers, are frequently utilized for a variety of medical applications. In one such application, the transducer is disposed at the end of an endoscope which is suitably positioned in the patient's esophagus for scanning such internal organs as the heart. When used in this manner, this transducer or probe is referred to as a transesophageal probe and the procedure is referred to as transesophageal echocardiography (TEE) when the probe is utilized for scanning the heart. Other invasive probes which have similar structures and requirements include transrectal, transnasal and transvaginal probes. The shaft of the endoscope serves as an enclosure for electrical and mechanical cables which couple the transducer and other electrical components of the endoscope to an external power source and external controls. Since a probe of this type and its shaft is positioned inside the body, the probe and shaft must be sealed to protect them against attack from bodily fluids and acids, as well as against sterilizing solutions and cleaning solutions either inside or outside the body. Moreover, the probe and shaft must protect the patient from currents carried by the electrical cables. Thus, the transducer as well as the shaft of the endoscope must be enclosed within an insulative, protective outer covering. Such a covering also helps protect the body from irritation as a result of probe rotation.

Existing shafts of such transesophageal probes typically comprise an inner, convoluted metal core which provides the required crush resistance to the shaft; a stainless steel braided sheath which is constructed over this inner core; and a outer coating of an elastomeric material. The elastomeric material serves as an insulator to protect the patient from electric currents; a smooth, corrosion-resistant surface to facilitate the placement of the probe; and a cover to protect the mechanical and electrical components of the endoscope from damage by bodily fluids.

One of the major causes of failure of this type of probe shaft is the physical penetration of this outer elastomeric coating by the patient. Penetration can result from the teeth of the patient being clamped tightly about the shaft, or from the shaft being rubbed against the patient's teeth during insertion of the probe. Even with the most cut-through resistant, flexible coatings available, such as urethanes, eventually the coating is penetrated by the patient's teeth, or by wear and tear from other sources. These penetrations are exacerbated by exposure to stomach acid, cold sterilants and cleaning fluids commonly used in a clinical setting. Once the elastomeric coating is penetrated, there is a direct, electrically conductive path between the patient and the probe, thereby introducing a potential safety risk to the patient. Even a single small penetration of the outer elastomeric coating can provide a direct electrical path to the patient, once the probe has been inserted into the esophagus.

Another important consideration is proper and complete sterilization of the probe and probe shaft. Cuts in the elastomeric coating can allow bodily fluids or bacteria to become trapped therein, particularly if the probe shaft is bent in such a way as to press together the edges of the cut after entry of fluids or bacteria. In such instances, the sterilization process might not completely flush out such bodily fluids and destroy the bacteria and subsequent patients could be contaminated. Also, if the outer elastomeric coating is completely pierced, bodily fluids and bacteria could enter the space between the braided sheath and the outer coating and travel longitudinally along the length of the probe shaft. Such fluids and bacteria would become trapped and could survive conventional sterilization procedures.

In designing shafts for invasive bodily probes, particularly for transesophageal probes, it is important that the shaft diameter be as small as possible. This shaft is the major portion of the probe that occupies the esophagus of the patient during the examination, and larger diameter shafts create tremendous patient discomfort during insertion and use. Any solution to existing problems of sterilization and penetration of the outer elastomeric coating by the patient should not significantly increase the outer diameter of the shaft. Thus, merely making the outer covering thicker is not a viable solution to these problems. Also, a thicker outer covering does not significantly reduce the likelihood of cut-throughs. It is also important not to significantly alter the inner diameter of the shaft, or the diameter of the metal core. The core diameter defines the space available for containment of the electrical and mechanical cables, and the demands of the probe place severe restrictions on the amount to which the diameter of the core can be reduced.

An improvement on existing probe shafts and one solution to the foregoing problems is found in U.S. Pat. No. 5,156,155, issued in the name of the applicant herein and assigned to the assignee of the present application. In U.S. Pat. No. 5,156,155, the conventional transesophageal probe shaft is modified to include a dielectric sleeve which is disposed between the core and sheath for electrically isolating the core from the sheath. A dielectric spacer is also provided in conjunction with a fitting disposed at the end of the shaft which completely seals the core from other portions of the probe to protect the patient from electrical currents carried by wires within the core and to protect the wires from damage from bodily fluids and cleaning solutions.

SUMMARY OF THE INVENTION

The foregoing and other problems are overcome in accordance with the present invention which relates to a shaft for an invasive bodily probe, particularly a transesophageal probe, which protects the probe from damage, prevents trapping of bodily fluids, and avoids any risk of injury to the patient, even if the outer coating is penetrated by the patient during use, without significantly altering the outer or inner diameters of the shaft.

The shaft of the present invention includes a crush-resistant core, a stainless steel braided sheath wrapped thereabout, and a very thin membrane disposed about the braid. The entire structure is coated with a tough elastomeric material. The membrane comprises a laminate of a textile layer disposed between two layers of a flexible film formed of a tough material, such as a urethane. The elastomeric material typically is adhered to the membrane along its length by an adhesive. In a preferred embodiment, to prevent the introduction of any bodily fluids, all of the interstices of the textile layer are filled with the flexible film such that no air pockets exist and no longitudinal movement of fluids along and through the textile layer of the membrane is permitted. While a patient may be able to bite through the outer elastomeric coating, the patient's tooth would be prevented from cutting entirely through the membrane because of the presence of the textile layer. Thus, the patient will never actually come into electrical contact with the core or braid and no fluids will become trapped. The membrane typically has a thickness of the order of 5 mils, so that the inner diameter of the shaft is unaffected, and the outer diameter of the shaft is only minimally increased.

In the preferred method of this invention, the membrane typically is formed by applying heat and pressure to a composite formed of a very thin textile layer disposed between the two layers of film so that the film material fills the interstices of the textile layer. The resulting laminate is formed into a tubular shape and heat sealed to itself along a seam. This tube is then pulled-over an existing cable, prior to application of the elastomeric coating.

BRIEF DESCRIPTION OF THE DRAWINGS

The objects, advantages, and features of this invention will be more clearly appreciated from the following detailed description when taken in conjunction with the accompanying drawings in which:

FIG. 5 is a partially cutaway, partial cross-sectional side view of the fittings of the probe shaft of the present invention; and FIG. 6 is a partial, cross-sectional side view of one of the fittings of the probe shaft of FIG. 5.

DETAILED DESCRIPTION OF THE PREFERRED EMBODIMENTS

Figure 1:
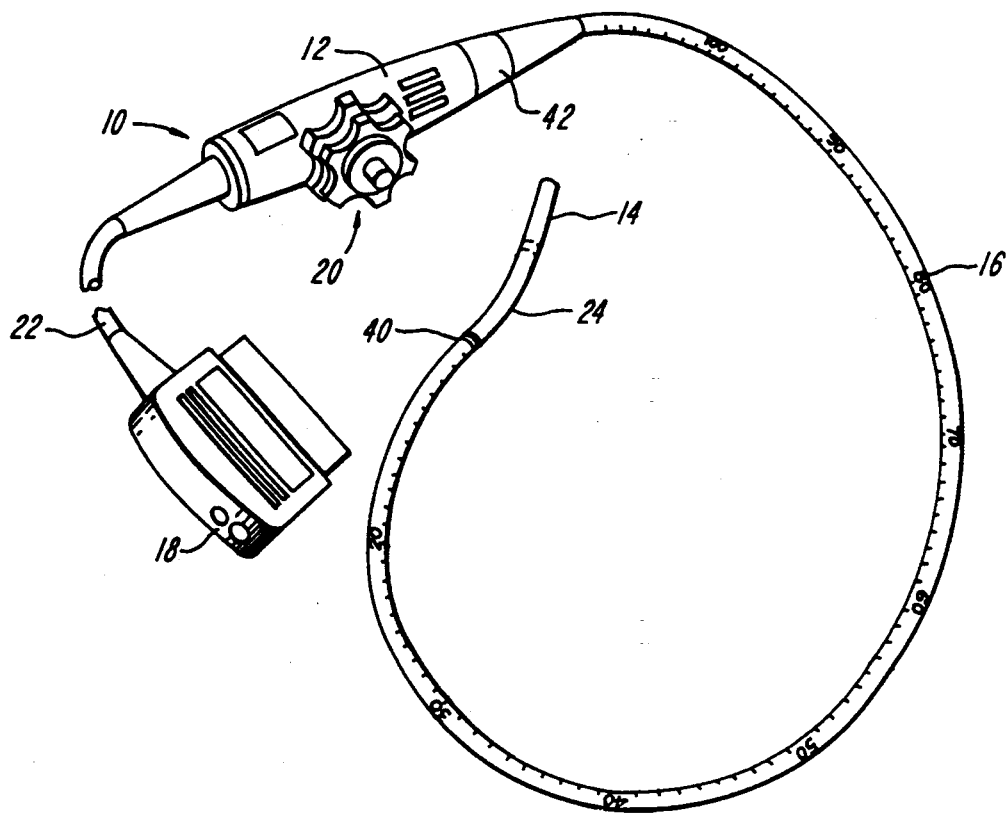
FIG. 1 is a pictorial representation of a transesophageal probe utilizing the shaft of the present invention.

With reference now to the drawings, and more particularly to FIG. 1 thereof, there is shown a pictorial representation of a typical transesophageal probe 10 with which the shaft of the present invention is to be used. Probe 10 is an ultrasonic probe suitable for insertion into a particular bodily cavity or orifice, namely the esophagus or the mouth. It is to be understood that this invention is being described with reference to a transesophageal probe for purposes of illustration only, and that this invention has equal applicability to other invasive bodily probes which utilize a shaft which must be protected from damage, and which must be electrically insulated from the patient, such as transrectal, transnasal and transvaginal probes.

Probe 10 includes a proximal head portion 12, a distal tip portion 14, a somewhat flexible shaft 16 connecting head portion 12 with distal tip portion 14 and electrical connector 18. Shaft 16 may include a flexible portion 24 adjacent distal tip portion 14 which can be bent. Distal tip portion 14 typically includes a transducer (not shown), and electrical cables 22 travel from connector 18, through head portion 12 and shaft 16 to the transducer. Typically, distal tip portion 14 can be deflected for proper positioning of the transducer by bending of portion 24. This deflection is produced by rotation of wheels 20 which are mechanically coupled to portion 24 by cables and the like (not shown) which travel through shaft 16. The manner of operation of transesophageal probe 10, and the details of its structure are well known to those skilled in the art, and need not be further discussed herein.

Figure 2:
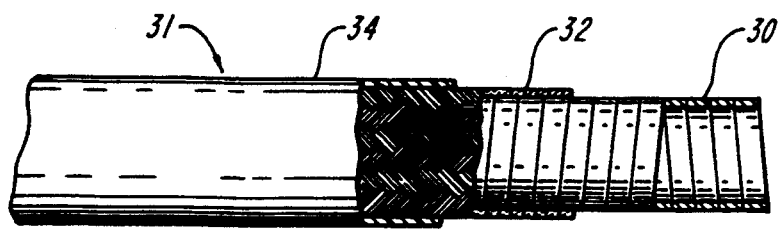
FIG. 2 is a partially cutaway, cross-sectional side view of a section of a prior art shaft.

A typical prior art shaft 31 is shown in FIG. 2. The prior art shaft of FIG. 2 comprises three components: an inner convoluted core 30, a stainless steel braided sheath 32 and an outer, elastomeric coating 34. As can be seen, sheath 32 is electrically coupled to core 30. Core 30 provides crush resistance to the shaft, and sheath 32 provides torsional stiffness. The stainless steel sheath is typically constructed over the inner core by feeding the core through a standard braiding machine. Outer elastomeric coating 34 typically comprises an extruded tube stretched over stainless steel sheath 32. In an alternative configuration, coating 34 may be dipped or brushed onto sheath 32. Elastomeric coating 34 both protects sheath 32 and provides a smooth, soft surface to the patient to prevent injury when inserting distal tip portion 14. Also, an elastomeric material can be easily sterilized, since it presents a smooth outer surface lacking any crevices in which bacteria can hide.

During use of the transesophageal probe 10, distal tip portion 14 is inserted into the patient's mouth and down his esophagus to be positioned therein for scanning of the heart or other bodily organs. During this process, some abrasion of the outer surface of shaft 16 can occur, and the patient could inadvertently bite down on shaft 16 during the process. Should a patient puncture coating 34 of shaft 31, he could become electrically connected to the electrical cables passing from connector 18 to distal tip 14. Furthermore, gastric juices and the like could penetrate sheath 32, and enter the interior of core 30, thus possibly damaging the mechanical and electrical cables and other components passing therethrough and rendering shaft 16 difficult to properly sterilize.

Figure 3:
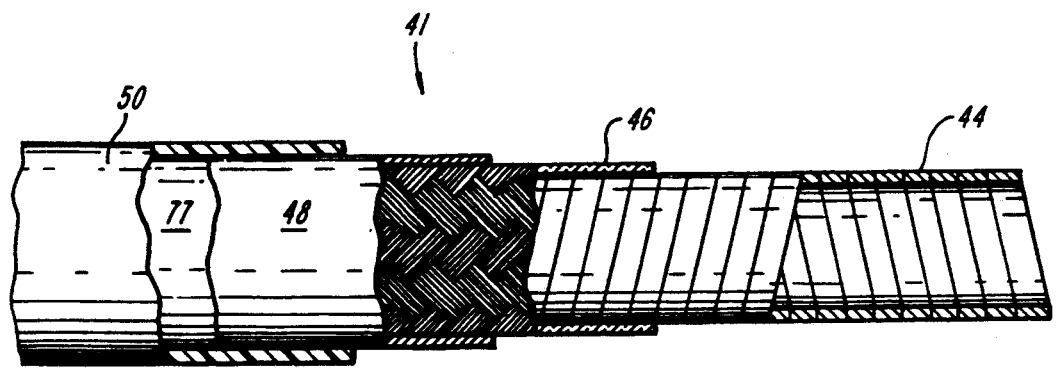
FIG. 3 is a partially cutaway, cross-sectional side view showing the probe shaft of the present invention.

Shaft 41 of the present invention, which comprises at least a portion of shaft 16, will now be described with particular reference to FIGS. 1 and 3. Shaft 41 extends between fittings 40 and 42, which assist in securing shaft 41 to adjacent sections of probe 10. Fitting 40 typically is disposed immediately adjacent portion 24, while fitting 42 typically is disposed in head portion 12, although either fitting may be disposed at other positions along shaft 16, the actual locations depending on the length of shaft 16 for which it is necessary that the core be electrically insulated from the patient.

Shaft 41 includes an inner convoluted core 44, a stainless steel sheath 46 surrounding core 44, a membrane 48 surrounding sheath 46 and an outer, tough, elastomeric coating 50 covering membrane 48. Core 44, sheath 46 and coating 50 may be similar to core 30, sheath 32 and coating 34, respectively, of shaft 31. Core 44 typically is composed of stainless steel, while sheath 46 typically is formed of braided stainless steel.

However, it is to be understood that core 44 may be composed of other materials besides stainless steel, so long as the required strength, rigidity and structural support are provided to prevent crushing of the core. Similarly, while a stainless steel braid is preferred for sheath 46, another similarly corrosion resistant, strong, durable material could be used. Also, while an elastomeric material is preferred for coating 50, other equally durable, corrosion resistant, dielectric materials could be utilized.

Figure 4:
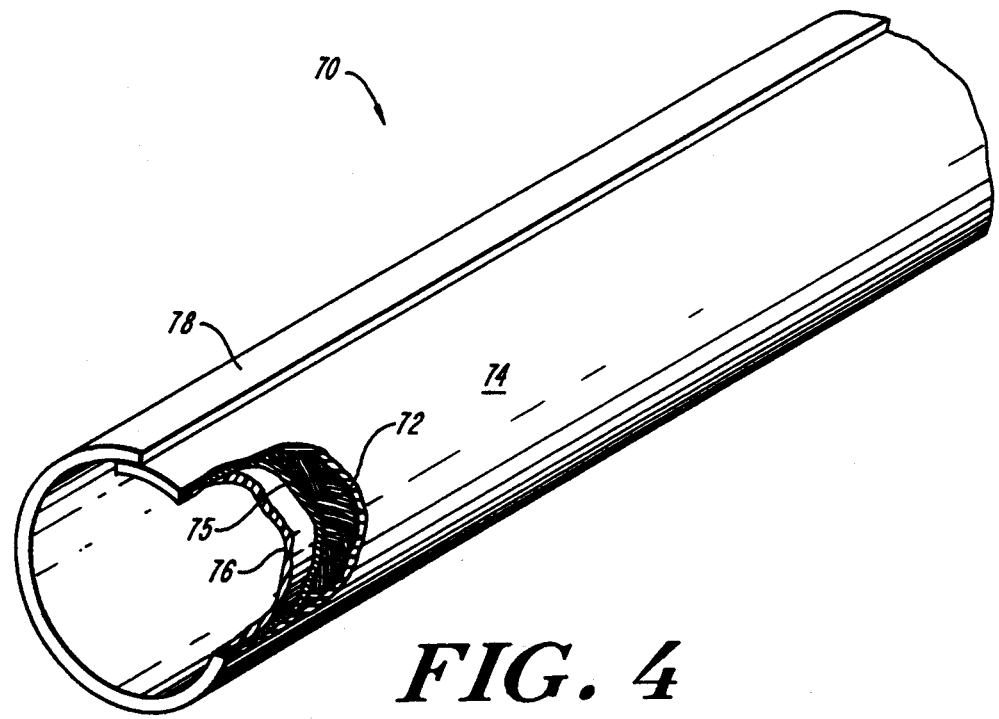
FIG. 4 is a partially cutaway, cross sectional, perspective view showing the structure of the membrane of this invention.

Membrane 48 will now be described with particular reference to FIG. 4. Membrane 48 is formed of a dielectric material which provides both electrical insulation and cut-through strength in very thin layers. Membrane 48 preferably is formed into a tube 70, as shown in FIG. 4. A typical tube 70 includes a laminate formed of central textile or fabric layer 72 disposed between an outer layer 74 and an inner layer 76. Preferably, layer 72 is encapsulated in layers 74 and 76. Layers 74 and 76 are formed from a flexible, tough, electrically insulative film. Preferably, layers 74 and 76 are formed of a material which can be caused to flow under heat and pressure or which can be compression molded. In a preferred embodiment, both outer layer 74 and inner layer 76 are formed of a plastic, such as urethane.

Layer 72 typically is a thin textile which provides the necessary reinforcement and which can be laminated between two layers of film. Layer 72 can be a woven, knitted, or non-woven textile, although a woven textile is preferred. Layer 72 can be formed of polyaramid, cotton, wool, polyester, nylon, glass or polypropylene fibers. The preferred material is a polyaramid, such as Kevlar®. Layer 72 preferably has an open structure with interstices 75 so that, under heat and pressure, layers 74 and 76 flow into the interstices 75 of layer 72 without trapping any air. Interstices 75 are thus completely filled with the material of layers 74 and 76. The result is a permanent laminate which is as thin as possible and into which no bodily fluids can enter or travel longitudinally. A preferred structure for layer 72 is one where interstices 75 comprise 30%–50% of the total area of layer 72 prior to encapsulation.

In a preferred embodiment, layers 74 and 76 are approximately 1–2 mils thick prior to bonding, and layer 72 is about 2–4 mils thick prior to bonding. The resulting thickness of the walls of tube 70 is preferably about 5 mils.

Fittings 40 and 42 couple shaft 41 to adjacent sections of probe 10 in a conventional manner. Exemplary fittings 40 and 42 are illustrated in FIGS. 5 and 6. Fitting 40 is secured to portion 24 at one end and to shaft 41 at the other end. Fitting 40 typically is circular in cross-section and includes a plurality of coaxial, stacked cylindrical sections 81, 82 and 84 which have successively reduced diameters. Typically, shaft 41 is secured thereto by attaching core 44 to section 84, such as with solder 95 and sheath 46 to section 82, such as with solder 97. Membrane 48 is bonded or adhered, such as by adhesive layer 83, to sheath 46 adjacent fitting 40. Section 81 is attached to portion 24 in a conventional manner. Typically, section 81 is attached to portion 24 using a plurality of linkages (not shown) connected to section 81 in a swivel manner to permit flexibility in portion 24. The linkages may be connected by rivets which allow adjacent linkages to pivot in orthogonal directions.

Fitting 42 is secured to head portion 12 of probe 10. Fitting 42 typically also is circular in cross-section and comprises a plurality of coaxial, stacked cylindrical sections 86, 88 and 90 which have successively reduced diameters. The outer surface of section 86 is provided with threads 87 for threadably coupling section 86 to head portion 12. Core 44 is bonded to section 90, such as with solder 95, while sheath 46 is bonded to section 88, such as with solder 97. As with fitting 40, membrane 48 is adhered or bonded to sheath 46, such as by an adhesive layer 83.

In one embodiment, as shown in FIGS. 5 and 6, the outer surface of coating 50 may be wrapped with threads 92 about section 82 of fitting 40 and/or about section 88 of fitting 42. Threads 92 are covered with epoxy 94 or the like for protection. Such a thread tie-down assures a secure, air tight and water tight seal.

To insure complete sealing so that sheath 46 and core 44 are completely isolated, preferably a layer of adhesive 77 is applied between coating 50 and membrane 48 all along the length of membrane between couplings 40 and 42. An acceptable adhesive is a urethane-based adhesive.

The method of formation of tube 70 will now be described with particular reference to FIG. 4. A flat sheet of the film forming either layer 74 or 76 is placed on a flat surface and cut to a dimension sufficient in length and in width for formation of the resulting tube. Typically, this film has a thickness of about 1–2 mils. A layer of a textile intended to form layer 72 of tube 70 is then placed in a planar configuration on top of the sheet of film. This textile layer preferably has a thickness of about 2–4 mils. Finally, a suitable flat sheet of film which corresponds to either layer 74, or layer 76 is placed on top of the textile. Layers 74 and 76 may be of the same material, or of a different material, so long as both layers 74 and 76 have the same softening or melting point.

Heat and pressure are then applied to this composite in a planar configuration. This heat and pressure may be applied by a typical compression molding press, or a typical calendar-roll process using large heated rolls. The distance between the rolls typically is accurately adjustable. Sufficient heat is applied to bring the materials to a temperature where the films forming layers 74 and 76 are flowable. If urethane is used, the desired temperature is about 300° F., and the pressure applied should be at least 100 psi. The composite is compressed sufficiently that preferably, interstices 75 are completely filled with the film materials to form the desired air-free laminate in which the textile layer is completely encapsulated within the material forming layers 74 and 76. The resulting thickness is less than that of the combination of the thickness of the two films and the thickness of the textile. The resulting laminate is removed from the press or calendar-rolls after about five minutes and is allowed to cool. The width of this composite is trimmed to equal the desired circumference of the resulting tube 70, plus about a ⅛" [0.125"] flap to allow formation of seam 78 for sealing of the tube along its length. Seam 78 is formed on a typical film-sealing machine and is liquid-tight.

The method of formation of shaft 41 of this invention will now be described with reference to FIGS. 3 and 4. First, core 44 is formed in a conventional manner by wrapping a strip of stainless steel or the like about a mandrel, as is well known in the art. Thereafter, in accordance with conventional assembly techniques, sheath 46 is constructed over core 44 by feeding core 44 through a standard braiding machine. Thereafter, previously-formed tube 70 is slid over sheath 46 and core 44. If tube 70 has been constructed with the desired tolerances, the result should be a tight fit between membrane 48 and sheath 46. This particular step can be incorporated into standard probe shaft manufacturing systems with little or no modification to the existing machinery.

Thereafter, outer coating 50 is applied. Coating 50 can be applied using one of two conventional techniques. In one process, a continuous plastic tube is formed by a conventional plastic extrusion machine. This tube has a diameter which is slightly less than the outside diameter of membrane 48 when wrapped about sheath 46. A porous metal tube, which is slightly larger in diameter than the outside diameter of the extruded plastic tube, is positioned within an outer, non-porous metal tube, and the ends of the outer tube are sealed. A vacuum line is connected to the outer tube, which permits a vacuum to be applied over the entire surface area of the porous inner tube. This entire structure is heated to the softening temperature of the material forming coating 50, which is about 200° F. for a urethane. Next, the plastic tube is placed inside the porous metal tube and is allowed to rise to the temperature of the porous tube, such as 200° F. for a urethane. The resulting plastic tube is, thus, softened. If other materials are used for coating 50, room temperature may be adequate, depending upon the durometer of the material.

While being heated, both ends of the plastic tube extend beyond the heated porous metal tube. One end of the plastic tube is clamped or sealed, while the other end is cooled. A fitting is attached to the other or unsealed end of the plastic tube for application of air pressure of a few pounds per square inch into the interior of the plastic tube to expand the plastic tube against the porous metal tube. Thereafter, the air is turned off and the porous metal tube holds the plastic tube in place due to the applied vacuum. Next, a layer 77 of a suitable adhesive is applied to the entire outer surface of membrane 48. Thereafter, both ends of the plastic tube are cut away and the structure comprised of core 44, sheath 46 and membrane 48 is inserted into the plastic tube. The vacuum is released and the plastic tube collapses onto the underlying structure to form coating 50. Adhesive layer 77 bonds coating 50 to membrane 48 all along the length of membrane 48 to prevent fluids or bacteria from entering and becoming trapped in a space between membrane 48 and coating 50.

A second, conventional method for applying coating 50 is to paint onto membrane 48 a thermosetting plastic resin with the desired thickness and then to cure the resin. Such thermosetting resins typically are of low viscosity and can be spread at ambient temperatures. No heat or pressure is required for formation of coating 50 if such resins are used. Such resins are inherently bonded to membrane 48 during curing so that no adhesive layer 77 is required for this method.

Membrane 48 seals and insulates sheath 46 and core 44 all along the length of sheath 46 and core 44. Should coating 50 be penetrated, the patient must pierce membrane 48 before he comes into electrical contact with sheath 46. Membrane 48 is sufficiently strong and resistant to cut-through that even if the teeth of a patient penetrate outer layer 74, these teeth will not also penetrate both layer 72 and inner layer 76. Thus, the patient cannot become electrically connected with sheath 46 or core 44. Also, should gastric juices or the like penetrate coating 50, they are prevented by membrane 48 from reaching sheath 46 or core 44 or the electrical or mechanical components contained within core 44. Finally, no fluids or bacteria can become trapped in membrane 48 or travel between membrane 48 and coating 50. Thus, shaft 41 can be fully sterilized.

The use of membrane 48 provides the foregoing advantages, and yet, does not increase the inner diameter of shaft 41 and only minimally increases the outer diameter of shaft 41. Thus, patient discomfort is minimally affected and core 44 remains capable of carrying all the necessary electrical and mechanical cables. Also, the application of membrane 48 can be accomplished using existing machinery and with minimal modification to existing processes for forming probe shafts. Therefore, a manufacturer will incur little additional costs by adoption of the present invention.

In view of the above description, it is likely that modifications and improvements will occur to those skilled in the art which are within the scope of this invention. The above description is intended to be exemplary only, the scope of the invention being defined by the following claims and their equivalents.

What is claimed is:

1. A shaft for use with a probe adapted to invade a bodily cavity, said shaft comprising:

an inner, electrically conductive core having a length and defining a channel extending along the length of the shaft;

an outer, electrically insulative coating completely surrounding said shaft; and a membrane disposed between said core and said outer coating and having a length extending along at least a substantial portion of said length of said core, said membrane comprising a textile layer encapsulated within a flexible film, said coating being directly bonded to said membrane along substantially the entire length of said membrane.

2. A shaft as recited in claim 1 wherein said textile layer has interstices which comprise about 30%-50% of the total surface area of the textile layer prior to formation of said membrane.

3. A shaft as recited in claim 1 wherein said film is formed of a urethane.

4. A shaft as recited in claim 1 wherein said membrane has a thickness of the order of 5 mils.

5. A shaft as recited in claim 1 wherein said textile layer is formed of a woven material.

6. A shaft as recited in claim 1 wherein said textile layer is compression molded between two layers of film.

7. A shaft as recited in claim 1 further comprising a layer of adhesive disposed between said coating and said membrane.

8. An ultrasonic probe suitable for insertion into a bodily cavity or orifice, said probe comprising:

a distal tip portion containing a transducer;

a head portion containing means for adjusting the position of said distal tip portion; and a shaft coupling said head portion to said distal tip portion and having a central channel containing electrical and mechanical connections extending from said head portion to said distal tip portion, said shaft comprising:

a central core enclosing said channel, said core having a length, said core being sufficiently flexible to permit bending of said shaft but being sufficiently rigid to prevent collapse of said channel;

an electrically insulating membrane encircling said core and having a length extending at least along a substantial portion of said length of said core, said membrane comprising a textile layer encapsulated within a flexible film; and an electrically insulating, corrosion resistant, flexible material covering said membrane, said flexible material being directly bonded to said membrane along substantially the entire length of said membrane.

9. A ultrasonic probe as recited in claim 8 wherein said textile layer is compression molded between two layers of film, said two layers of film being formed of a plastic material which softens upon the application of heat.

10. A ultrasonic probe as recited in claim 8 wherein said membrane has a thickness of the order of 5 mils.

11. A method for forming a shaft for use with a probe adapted to invade a bodily cavity, said method comprising the steps of:

forming an inner, electrically conductive core having a length and defining a channel extending along the length of the core;

forming a membrane of a layer of a textile encapsulated within a flexible film;

applying the membrane to the core to completely encircle the core along the length of the core; and applying to the membrane a coating of an electrically insulating, corrosion resistant, flexible material, said coating extending along an entire length of the membrane and being directly bonded to the membrane along substantially its entire length.

12. The method as recited in claim 11, wherein said forming step comprises the steps of:

placing a layer of a textile having interstices between two layers of a flexible film;

applying heat and pressure sufficient to force the material of the film into interstices in the layer of textile to form a laminate;

forming the resulting laminate into a tube with a size which fits tightly over the core, said tube having a flap which extends along the length of the tube; and sealing the flap to the tube.

13. The method as recited in claim 12 wherein said membrane applying step comprises the step of pulling the tube over the core.

14. The method as recited in claim 12 wherein said heat and pressure applying step comprises the step of compressing the two layers of film and the layer of textile until the resulting thickness of the laminate formed is less than the combined thicknesses of the two layers of film and the layer of textile.

15. The method as recited in claim 12 wherein said heat and pressure applying step comprises the step of applying sufficient heat and pressure to the two layers of flexible film to cause the layers of film to flow into interstices in the layer of textile.

16. The method as recited in claim 11 further comprising the step of applying an adhesive between the membrane and the coating.

* * * * *